United States Patent [19]
Tailor et al.

[11] Patent Number: 5,624,386
[45] Date of Patent: Apr. 29, 1997

[54] THERMOPLASTIC ORTHOPEDIC BRACE AND METHOD OF MANUFACTURING SAME

[75] Inventors: Dilip K. Tailor, Brampton; Mark F. Lang, Oakville; Paul S. Hruska, Mississauga; Kevin J. McConnell; Beverly Lucek, both of Hamilton, all of Canada

[73] Assignee: Bay Mills Limited, Oakville, Canada

[21] Appl. No.: 332,976

[22] Filed: Nov. 1, 1994

Related U.S. Application Data

[63] Continuation-in-part of Ser. No. 196,925, Feb. 15, 1994, Pat. No. 5,529,826.
[51] Int. Cl.$^6$ ........................................ A61F 5/052
[52] U.S. Cl. .................. 602/16; 428/110; 602/5; 602/6; 602/26
[58] Field of Search .................. 602/5, 6, 16, 26; 428/110, 226, 294

[56] References Cited

U.S. PATENT DOCUMENTS

| | | | |
|---|---|---|---|
| 1,228,113 | 5/1917 | Hinson | 602/16 |
| 4,271,831 | 6/1981 | Deibert | 602/16 |
| 4,651,445 | 3/1987 | Hannibal | 36/103 |
| 4,697,583 | 10/1987 | Mason et al. | 602/16 |
| 4,770,838 | 9/1988 | Cattanach | 264/510 |
| 4,778,717 | 10/1988 | Fitchmun | 428/246 |
| 5,009,223 | 4/1991 | DeFonce | 602/16 |
| 5,022,391 | 6/1991 | Weidenburner | 602/16 |
| 5,082,701 | 1/1992 | Craven et al. | 428/34.5 |
| 5,135,469 | 8/1992 | Castillo | 602/16 |
| 5,286,249 | 2/1994 | Thibodaux | 602/6 |
| 5,328,446 | 7/1994 | Bunnell et al. | 602/16 |
| 5,476,441 | 12/1995 | Durfee et al. | 602/16 |

*Primary Examiner*—James C. Cannon
*Attorney, Agent, or Firm*—Duane, Morris & Heckscher

[57] ABSTRACT

Thermoplastic, thermoshapable composite laminate bars, an orthopedic brace using the shaped composite bars as integral components, and a method of thermoshaping the composite bars for use as fitted components in the orthopedic brace are provided. The composite bars contain multiple fiber layers oriented in at least two directions with respect to the bar length to provide high flexural and torsional strength. The novel method of thermoshaping yields improved results over prior thermoshaping methods by providing an uncomplicated shaping capability while maintaining the structural and mechanical properties of the composite bar.

11 Claims, 8 Drawing Sheets

THERMOPLASTIC ORTHOPEDIC BRACE AND METHOD OF MANUFACTURING SAME

CROSS-REFERENCE TO RELATED APPLICATION

This is a continuation-in-part of application Ser. No. 08/196,925, filed Feb. 15, 1994, now U.S. Pat. No. 5,529,826.

FIELD OF THE INVENTION

This invention relates to thermoplastic composite materials that are used as structural elements, and more particularly, to the use of thermoplastic composite materials as components for orthopedic bracing devices, and methods for manufacturing such components.

BACKGROUND OF THE INVENTION

The key elements of a traditional knee-brace or elbow-brace orthosis consist of two pairs of upright bars connected to a pair of hinges centered at the appendage joint; the respective pair of bars extend above and below the appendage joint to be supported; and the respective pairs of the bars are joined to each other with a band going around the half-circumference of the respective lower appendage (below joint) or the upper appendage (above the joint).

The upright bars have traditionally been made from metals, such as steel and aluminum, due to their excellent mechanical strength and modulus, and also due to their ability to be shaped without breaking, which allows the bar to be shaped to fit the patient's appendage. The fitting of a metallic bar to the patient's appendage or to the model cast of the appendage is done by mechanically bending and hammering the metal into shape through trial and error until a desired shape is achieved. Despite care and diligence it is difficult to obtain a completely precise conformance of the bar to the desired shape of the patient's appendage due to the very nature of the bending process, which is long and tedious, relying heavily on the craftsmanship of the technician. When a post-adjustment of the brace is necessary, the process of bending the bar or bars while on the brace is difficult if not impossible.

While the high strength and modulus of the metal provides the bar with excellent performance in being able to withstand high stress and impact loads sustained during usage of a brace, the high specific gravity of the metals makes the brace heavy and therefore uncomfortable to wear. Moreover, many patients requiring a joint orthoses concomitantly have weakened muscles. As such, carrying a heavy brace on the patient's appendage has the effect of contradicting the original intention of the brace—minimizing loads and supporting the weakened appendage and joint.

As an alternative to metal, orthosis brace bars could be fabricated from lightweight composite materials. Fiber reinforced plastic composites have traditionally been made from thermoset resins such as epoxy and polyester. The basic technique involves saturating the fibers or fabric with a liquid resin and then curing or cross-linking the resin to harden it. The cured finished thermoset composite cannot be reheated, softened and shaped.

Attempts have also been made to produce a bar with a partially cured thermoset composite, so that a flat laminate bar could be formed in its soften state, and then shaped. This is a cumbersome process requiring sophisticated, expensive machinery. Moreover, even with this machinery, the results are mixed. Because the bar cannot be resoftened after the final curing, post adjustment of the bar is impossible. For most patients, post-fitting adjustment of the brace is necessary.

While bars made with thermoplastic resin do provide repeated thermoshaping capability, they do not have the required mechanical performance. This is particularly true due to the low flexural strength and low flexural modulus of bars made solely with thermoplastic resin. The desired mechanical performance, however, could be obtained by using high strength and high modulus fibers such as carbon, glass or quartz fibers. Combining these fibers with suitable thermoplastic resin could provide a composite with desired mechanical properties and thermoshaping capabilities. Attempts have been made at making the upright bar using short fibers or discontinuous fibers by pultrusion, injection molding or compression molding. However, discontinuities in the fiber length naturally induce weaknesses in the bar, because the strength of the bar structure becomes critically weakened at the fiber length discontinuities.

Although thermoplastic composites do allow for repeated readjustments, in the application of a composite fiber layer laminate, the heating and shaping results in several problems. The dimensions of the bars generally used for orthosis braces are usually in the range of 16 mm×4 mm (width× thickness), 18 mm×5 mm, and 22 mm×6 mm. The ratio of width to thickness typically is 3:1 to 4:1, or alternatively, the bar thickness is approximately 25% to 30% of the width. These dimensions for a composite laminate bar raise several problems relating to the process of heating and shaping the bar.

For example, when the bar is heated, e.g., in an oven, to the melting point of the resin and formed into a shape with a moderate 50 mm radius curvature, several undesirable effects occur to the bar. First, the composite has a tendency to loft, i.e., increase in thickness, due to relaxation of stresses in the compressed laminate. The layers may tend to separate and the overall bar shape generally distorts, that is, it does not remain flat and maintain a rectangular shape.

In order to "reconsolidate," the softened bar into the flat, rectangular shape and recompress the lofted composite layers, uniform pressure needs to be applied to the bar in a controlled way. This is extremely difficult to do. It is found that when a heated bar is shaped with any kind of pressure, the pressure is unevenly imparted to the bar, causing the bar layers to slide and lose the desired rectangular shape. When pressure is applied to recompress the lofted bar, local distortion of the bar often occurs because the pressure is uneven. Accordingly, reconsolidation leads to deformed and unacceptable bars.

Figure 11A:
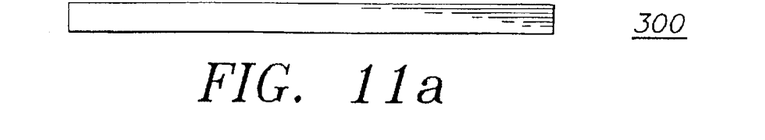
FIGS. 11–11(a): are side views of a composite bar illustrating the shaping of the bar where the fiber-containing layer lengths change as the bar is shaped.
Figure 11B:
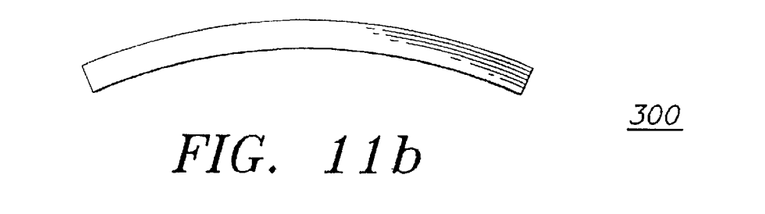
Figure 12:
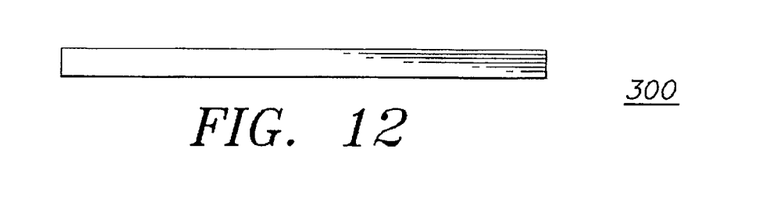
FIGS. 12–12(b): are side views of a composite bar illustrating the different results of shaping the composite bar where (a) the fiber-containing layer lengths do not change— the bottom layers wrinkle, and (b) the fiber-containing layers slide with respect to each other.
Figure 12A:
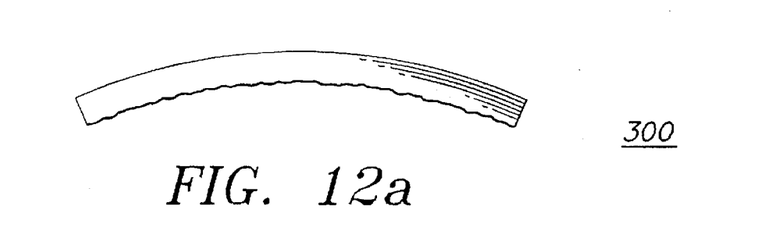
Figure 12B:
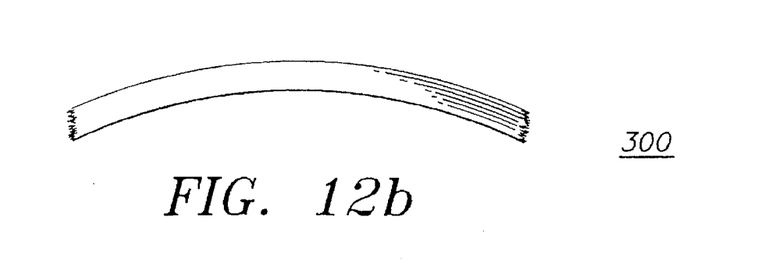

Another phenomenon complicating the shaping process is the physical difference in the length of the top surface and bottom surface of a bar shaped into an arc, as shown in FIG. 11(b). The bottom surface naturally is shorter in length than the top surface. However, because the fiber-containing layers cannot alter in length, the bottom surface either wrinkles and buckles, or the fiber-containing layers slide in the longitudinal direction in relation to each other as shown in FIG. 12(a) through FIG. 12(b).

In practice, wrinkling or buckling is unacceptable because such a result evidences a damaged product and is a weakness in the composite. Therefore, the sliding of the layers should be facilitated. However, in the shaping of a composite bar, the uncontrolled sliding of the fiber-containing layers results in disorientation of the fiber-containing layers.

The net result of the above described phenomena is that the shaped bar looses as much as 50% to 80% of its mechanical strength, in addition to having unacceptable aesthetic appearance for use as a brace.

Attempts have been made to control the shaping process by partially melting the resin, so that the shape does not distort easily. While this may result in a "good looking" bar, the strength of the bar is markedly reduced because the sliding of the layers is effectively prevented by some "unmelted resin." Moreover, cracks sometimes result in the bar laminate.

The prior art has also attempted the use of heat shrink tubing to contain the body of the bar. This results in an oval shaped bar because the tubing tends to shrink around the bar with concentric pressure. Moreover, the commonly available heat shrink tubing is soft at the melting temperature of the bar. The pliability of this softened tubing allows uncontrolled distortion of the bar during the shaping process.

Accordingly, there appears to be a need for a lightweight thermoplastic composite laminate bar with high modulus and flexural strength, that is repeatedly thermoshapable for use as the structural components in orthosis braces. There is also a need for a simple method of thermoshaping the composite bar that maintains the high modulus and flexural strength, and the aesthetic appearance of the unshaped bar.

SUMMARY OF THE INVENTION

A thermoplastic orthopedic brace, with thermoshapable bars and an easy method of shaping the bars as integral components in the brace are provided by this invention. The composite bars contain multiple fiber-containing layers oriented in at least two directions related to the bar length to provide high flexural and torsional strength. The novel method of thermoshaping the composite bars maintains the structural and mechanical properties, as well as the aesthetic appearance of the preshaped composite bar.

The thermoplastic orthopedic brace of this invention has the primary attributes of being lightweight, yet having the high mechanical strength required of a brace. The mechanical strength of the brace components, and therefor the strength of the brace itself, results from proper selection of fiber types and resins comprising the composite. For maximum strength, the fiber-containing layer, in all orientations, must continuously extend from one edge of the bar to the opposite edge. With these features, this invention overcomes the problems cited above with respect to heavy, metal orthopedic braces.

An orthopedic brace embodiment of this invention could be constructed using upright support bars connected to each other by shaped thermoplastic composite bars to form cradle structures. Two such cradle structures joined to each other by a mechanical joint may be held on the distal and medial portions of a person's appendage by retaining straps.

The method of shaping the composite bars for use as the structural components in the brace solves the above described problem of inability to readjust the brace after an initial fitting on the patient. Through this method, an easy way to fit an orthopedic brace to a patient's appendage is available.

With the invention method, thermoplastic composite bars can be easily shaped while retaining the pre-shaped structural properties and aesthetic appearance of the bar. The method relies on two components to form a mold used to retain the structure and mechanical properties of the pre-shaped bar. The two components are a pair of molding strips between which the composite bar is placed, and a taping means for tightly holding the molding strips in contact with the composite bar. The molding strips and taping means mold and maintain the rectangular shape and structural integrity of the thermoplastic composite bar during heating and shaping while allowing the fiber-containing layers to slide in relation to each other. This ability for the fiber-containing layers to slide during the shaping process prevents wrinkling and buckling of the layers that characterize defects in the bar.

BRIEF DESCRIPTION OF THE DRAWINGS

The accompanying drawings illustrate preferred embodiments of the invention so far devised for the practical application of the principles thereof, and in which.

DESCRIPTION LIST OF REFERENCE NUMERALS APPEARING IN THE DRAWINGS

10 Unidirectional Fiber Reinforced Thermoplastic Tape
12 Unidirectional Fibers
14 Thermoplastic Matrix
16 Seamed Sheet in 0°
18 Seamed Sheet in 90°
20 Seamed Sheet of Tape
30 Woven Sheet of Tape
40 Scrim
50 Woven Fabric
100 Polymer Matrix Composite Material
200 Orthopedic Brace
201 Orthopedic Brace Band
202 Upright Bar
203 Mechanical Joint
204 Flexible Strap
205 Orthotic Support
300 Thermoplastic Composite Bar
310 Composite Laminate Molding Strip
311 Fabric-Containing Layers For Molding Strip
320 Molding Strip
330 High Temperature Tape

DETAILED DESCRIPTION OF THE INVENTION

Fabric-Faced Thermoplastic Composite Panel

Polymer matrix composites are provided by this invention which contain fabric facing layers disposed on thermoplastic composite cores. These composite materials can be thermoformed to provide a smooth fabric surface which is virtually free of wrinkles, kinking, and buckling. As used herein, the term "thermoplastic" refers to any polymer resinous material or blend that softens upon heating and solidifies upon cooling and can be thermoformed by application of heat and pressure. The term "fabric layer" is a relatively broad term meant to encompass both woven and nonwoven fabric layers and scrims. Finally, the term "elasticity" means the ability of a material to distort elastically as result of the construction of the material or due the inherent tensile elongation properties of the plastic or fibers used in the material.

With reference to the Figures, and particularly to FIGS. 1–3 and 6 thereof, the thermoplastic composite core of this invention will now be described. The thermoplastic composite core includes a thermoplastic matrix containing a reinforcement, preferably reinforcing fibers, and also singular layers of thermoplastics sandwiched in the composite core.

The thermoplastic matrix of the composite cores of this invention contain one or more thermoplastic resins, alloys or copolymers. Typical resins useful in this regard include acetal, acrylics, cellulosics, fluorocarbons, nylons, polyallomer, polyaryl ether, polyaryl sulphone, polycarbonate, polyethylenes, polyimide, polyphenylene sulfide, polypropylene, polystyrene, polyurethane, pollvinyl chlorides, styrene acrylonitrile, polyphenylene oxide, polysulfone, polyether sulfone, polymethylmetha acrylates, polyesters (PET, PBT), and their respective copolymers, compounds, and derivatives.

The preferred reinforcing fibers 12 of this invention are of the light-weight and high-strength high modulus variety, such as carbon, glass, aramid, metal, or ceramic fibers. These fibers are preferably uniformly distributed throughout the composite to about 10–80 vol. %, and preferably at least about 30% volume. Factors that influence the fatigue resistance and tensile properties of reinforced thermoplastics include the proportion of reinforcing fibers, morphology of the reinforcement (i.e. random chopped mat, unidirectional fiber, or woven cross-ply roving), and the matrix resin. For example, in carbon-reinforced composites, fatigue, and tensile performance of chopped-mat reinforcement is significantly lower than that of a woven, cross-ply fabric.

Advanced composites, such as unidirectional carbon/ thermoplastic laminates can have better fatigue resistance than steel, aluminum, or glass-reinforced composites. Compared with unidirectional laminates, the fatigue strengths of other reinforcement types in decreasing order are: 85% unidirectional, cross-ply, glass fabric, and randomly oriented short fibers. Accordingly, this invention prefers that the fibers are unidirectional and that the composite material contain a laminated structure. Discontinuous fibers more closely model the fatigue strength of the polymer matrix, making fiber-to-matrix bonding more important for optimum performance.

Presently, the preferred fibers of this invention comprise carbon, glass, such as E-glass and S-glass, boron, aramid, such as KEVLAR® 29 or KEVLAR® 49 (available from du Pont), ceramic fibers, metallic fibers, and metal coated fibers.

The above-described thermoplastic resins and reinforcing fibers can be arranged in a number of variations to produce dozens of thermoplastic-fiber composites. Some of these variations are described, along with their resulting fatigue properties, in Table I below:

TABLE I

| Material cycles | Fatigue Strength of Reinforced Thermoplastics[1] | | | |
|---|---|---|---|---|
| | Glass fibers, % | Carbon fibers, % | Strength, $\times 10^3$ psi | |
| | | | @ $10^4$ cycles | @ $10^7$ |
| Acetal Copolymer | 30 | — | 9 | 7 |
| Nylon 6[2] | 30 | — | 7 | 5.7 |
| Nylon 6/6 | — | — | 6 | 5 |
| Nylon 6/6[2] | — | — | 3.4 | 3 |
| Nylon 6/6[2] | 30 | — | 8 | 6 |
| Nylon 6/6[2] | 40 | — | 9 | 7 |
| Nylon 6/6 | 40 | — | 10.5 | 9 |
| Nylon 6/6[2] | — | 30 | 13 | 8 |
| Nylon 6/6[2] | — | 40 | 15 | 8.5 |
| Nylon 6/10[2] | 30 | — | 7 | 5.5 |
| Nylon 6/10[2] | 40 | — | 8 | 7 |
| Polycarbonate | 20 | — | 9 | 5 |
| Polycarbonate | 40 | — | 14.5 | 6 |
| Polyester, PBT | 30 | — | 11 | 5 |
| Polyester, PBT | — | 30 | 13 | 6.5 |
| Polyetheretherketone | — | 30 | 18 | 17.5 |
| Polyethersulfone | 30 | — | 16 | 5 |
| Polyethersulfone | 40 | — | 19 | 6 |
| Polyethersulfone | — | 30 | 22 | 6.7 |
| Mod. Polyphenylene Oxide | 30 | — | 7 | 4.7 |
| Polyphenylene Sulfide | — | 30 | 13 | 9.5 |
| Polysulfone | 30 | — | 14 | 4.5 |
| Polysulfone | 40 | — | 16 | 5.5 |

[1]Tests by ASTM D 671 at 1,800 cycles/min., as reported in Advanced Materials & Processes, Vol. 137, Issue 6, p. 102 (June 1990).
[2]Moisture conditioned, 50% R.H.

The thermoplastic composite core of this invention can be fabricated in a number of ways. One method is to begin with continuous rovings or bundles of fibers. The rovings are spread out to separate the filaments and then they are passed through a fluidized bed of thermoplastic resin powder. The spread fibers pick up the powder as they pass through the fluidized bed. The now resin-coated fibers are heated to the melting point of the thermoplastic resin in an oven to smoothly coat the fibers to wet them out completely, or as nearly completely as the process permits. Since the now-coated fiber bundle is in a nongeometric shape, it is then passed through a die or former to shape the bundle into a tape-like configuration. This tape preferably has a width which is much greater than its thickness. The thickness should be at least 50 μm so as to have sufficient strength to withstand mechanical working into the final thermoplastic matrix, and a preferred width of at least about 3 mm to avoid over twisting during the subsequent mechanical operations.

Alternatively, the fibers may be passed through an extrusion cross-head die containing a bath of molten thermoplastic polymer. As the fibers pass through the die, the molten polymer coats the fibers and completely wets them out. This operation could also be followed by a shaping step to configure the coated bundle of fibers into a tape configuration. Other methods include passing the fibers through a solution in which the polymer powder is suspended, or sandwiching the fiber web between films of polymer, and then passing them through heated laminated rollers under pressure and elevated temperature to coat them. Both of these fabrication methods can be additionally followed by a forming step to produce tapes.

Figure 1:
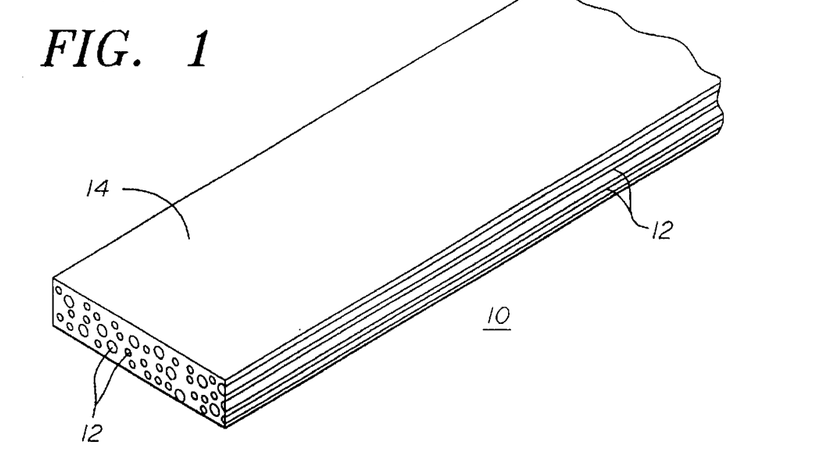
FIG. 1: is a front perspective view of a preferred unidirectional fiber reinforced thermoplastic composite tape of this invention.
Figure 2:
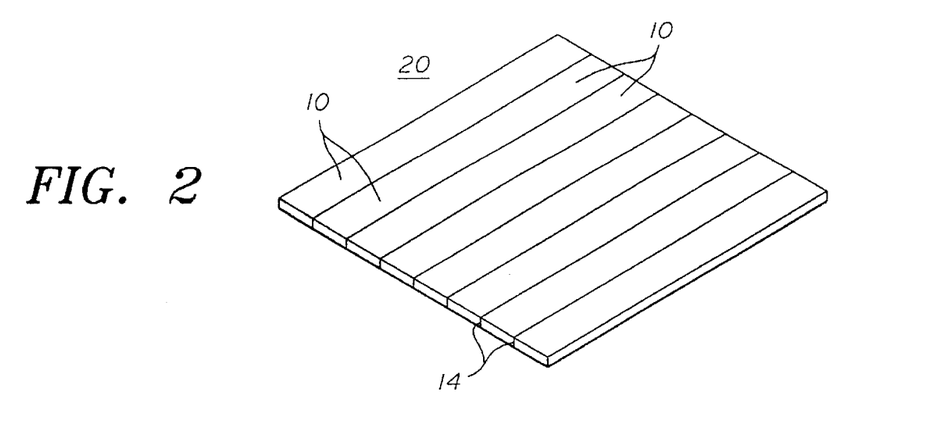
FIG. 2: is a front perspective view of a composite sheet composed of a plurality of the composite tapes of FIG. 1 which have been seamed together along their longitudinal sides.

The end result of these impregnation methods is that a tape 10 is formed in which there are continuous unidirectional fibers 12 in the axial or longitudinal direction, and that these fibers 12 are encapsulated within a thermoplastic, thermoformable matrix 14, as substantially described in FIG. 1.

Figure 3:
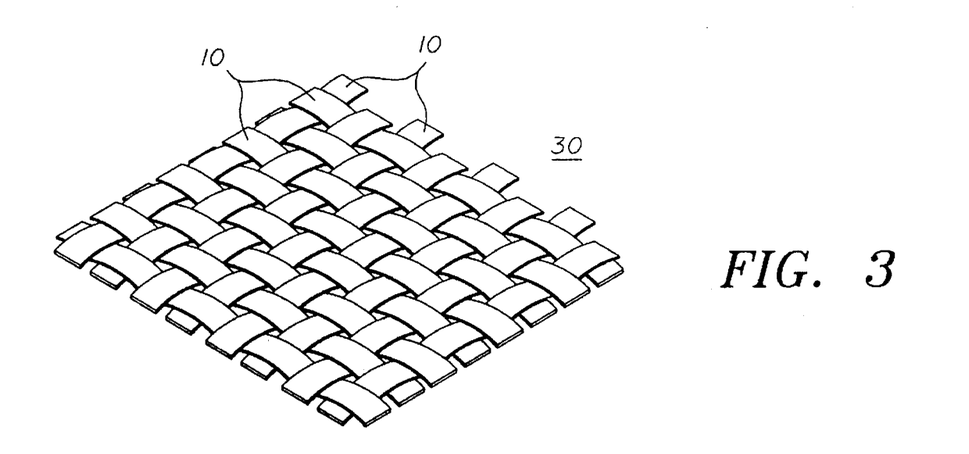
FIG. 3: is a top perspective view of an alternative composite sheet illustrating a plurality of composite tapes of FIG. 1 woven to form a fabric.

In order to produce a panel from these unidirectional fiber reinforced thermoplastic tapes 10, a plurality of tapes can be woven into sheet fabric, such as woven sheet of tape 30, shown in FIG. 3. In this woven sheet 30, the tapes 10 are oriented in the 0° and 90° direction. Such woven constructions are disclosed in U.S. Pat. No. 5,082,701, which is hereby incorporated by reference. Alternatively, the tapes can be placed adjacent to one another and seamed, attached, welded, or stitched in position before laying the next tape 10 as shown by seamed sheet 20 of FIG. 2.

In an alternative procedure for constructing panels, a "commingled fiber fabric" is produced. Fibers or thermoplastic resin and reinforcing fibers are comingled into a yarn. The commingled yarns are then woven into fabric. The fabric or layers of fabric are compression molded into a flat laminate under heat and pressure. The resin fibers melt and flow to wet out the reinforcing fibers.

In still another method, an "assembled composite" can be produced. In such a method, woven or nonwoven fabric random or directional webs of reinforcing fibers are alternately stacked with a layer of thermoplastic film or powder. This assembly is then consolidated into a laminate under heat and pressure. Also, the method described by Fitchmun, U.S. Pat. No. 4,778,717 whereby a fabric is dipped in a liquid resin may be employed.

Figure 6:
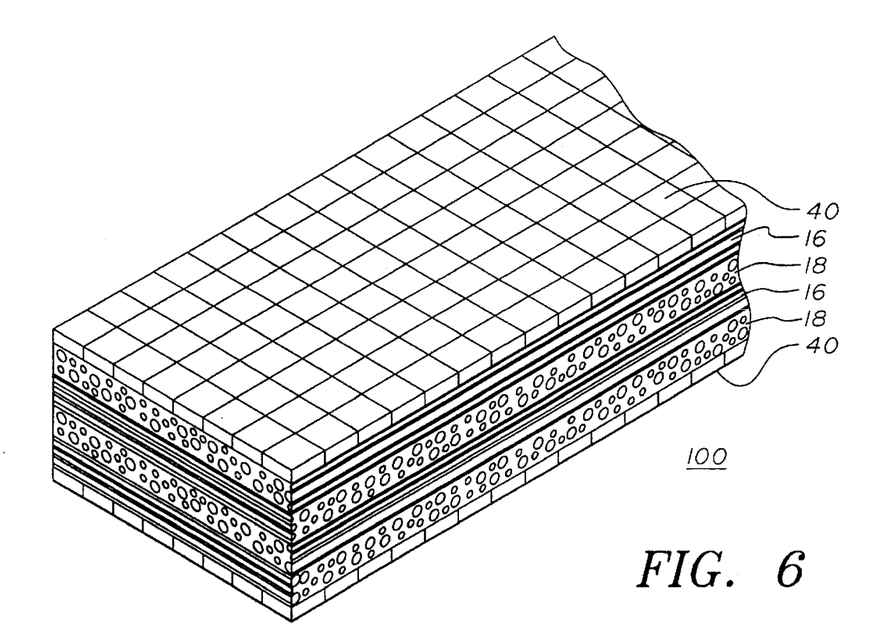
FIG. 6: is a top perspective view of a preferred polymer matrix composite of this invention including a laminated, thermoplastic composite core and a pair of fabric facing layers.
Figure 7A:
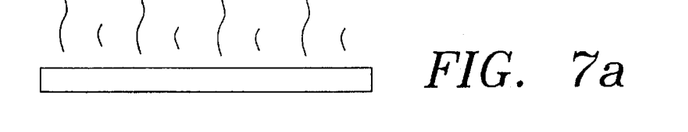
FIGS. 7(a)–(d): diagrammatically illustrate a preferred thermoforming sequence for preparing molded articles pursuant to this invention.
Figure 7B:
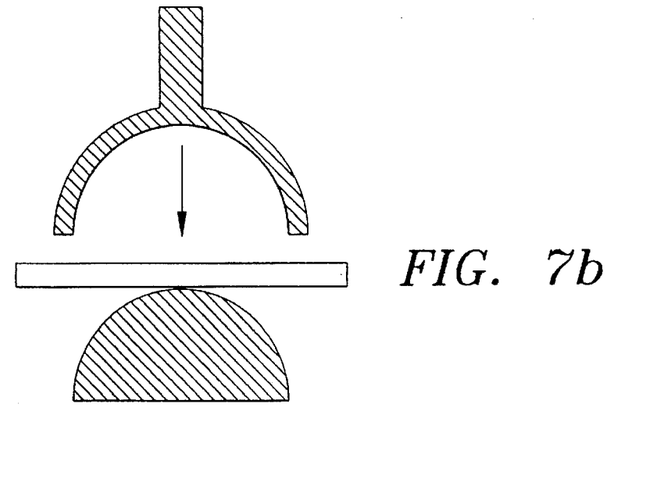
Figure 7C:
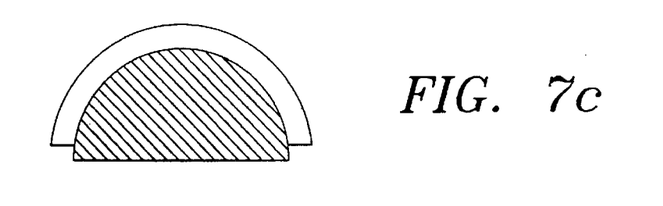
Figure 7D:
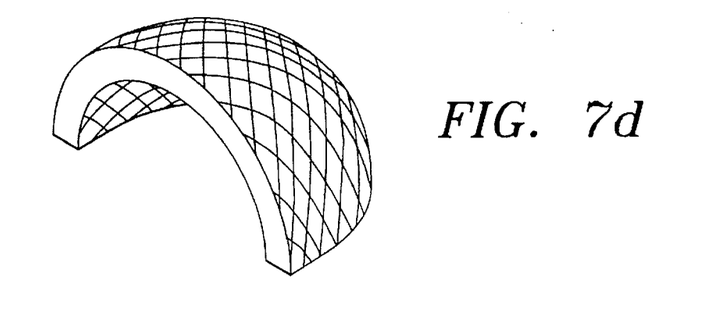

Referring to the polymer matrix composite material 100, shown in FIG. 6, it will be understood that the preferred thermoplastic composite core is produced by laminating at least two thermoplastic sheets comprising unidirectional fibers having different orientations. These sheets are desirably placed on top of one another; for instance in a 0°/90°/0°/90° orientation that would be functional. However, it will be understood that there are numerous orientations and ply combinations.

The sheets used in the thermoplastic composite core in this embodiment can be thermoformed to laminate them together into a integral composite. In one manufacturing sequence, the laid up sheets are placed in a compression molding press, where heat and pressure are used to consolidate the assembled sheets into a nearly void-free solid composite laminated panel. It is envisioned that both seamed sheets 20 and woven sheets 30 can be used interchangeably in the laminated construction. Alternatively, comingled fibers fabric or the assembled composite (described above) can be incorporated into the structure of the laminated composite panels.

Additionally, a thin thermoplastic film can be placed on both sides of the laminated composite, particularly if the top laminated sheets contain woven tapes, to fill in any voids resulting in the lamination of the woven pattern. The polymeric ingredients disclosed for the matrix of the thermoplastic composite core would be suitable resins for this film.

Figure 4:
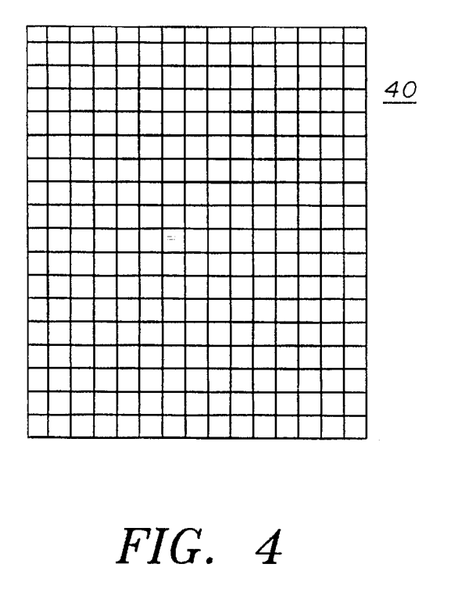
FIG. 4: is a top planar view of a reinforcing scrim.

The preferred fabric layer 40 of this invention will now be described. Although woven and nonwoven fabrics and scrims are suitable for this invention, woven fabrics are the most desirable. A fabric 40, such as that described in FIG. 4, is a nonwoven fabric, screen of bonded fibers or a woven fabric, whereby the construction permits the yarns or individual fibers to move relative to their intersection points.

The fabric layer of this invention does not necessarily need to contribute to the mechanical properties of the panel, therefore it does not have to, but may, contain high strength fibers, such as those types of fibers reinforcing the thermoplastic composite core. Instead of carbon, glass, or aramid fiber, the fabric layer 40 of this invention preferably contains ordinary, natural, or synthetic fibers, such as cotton, wool, silk, rayon, nylon, polyester, polypropylene, polyethylene, etc. The advantage of using these traditional textile fibers, is that they are available in many colors and can provide an infinite variety of patterns and textures to the preferred fabric layers. Such fibers can be woven, or spunbonded to produce nonwoven textile fabrics. Alternatively, plain color fabric can be easily dyed and printed in a variety of colors and patterns. Additionally, reinforcing fibers, such as glass, carbon, and aramid, could be used for surface fabric, provided the overall fabric construction allows sufficient elasticity.

Figure 5:
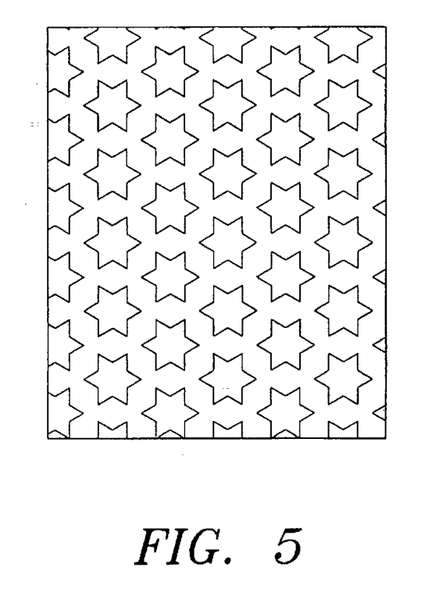
FIG. 5: is a top planar view of a printed fabric.

As described in FIG. 5, the preferred woven fabric 50 can include a printed, aesthetically appealing printed pattern. The pattern can be created by weaving different colored fibers into an ornamental design, however, this would involve using numerous yarn inputs with different colors in the warp, and complex weft inputs to obtain sophisticated patterns. A less expensive alternative would be to use commercially available patterned fabrics, which are intended for garments or furniture, etc., and apply these fabrics to the thermoplastic composite core of this invention. Accordingly, this invention prefers to employ consumer textile fabrics, imprinted with art work, logos, and trademarks which are printed, dyed, or silk screened onto the fabric.

The fabric layers of this invention are preferably bonded to the resin-containing thermoplastic composite core with a "resinous adhesive", e.g. film, powder, or tacky material used to bond the fabric to the core. One preferred method of applying the fabric layer to the core is to prepare a thin film, 10 μm to 500 μm thick, made from a compatible thermoplastic resin as the matrix of the thermoplastic composite core. This film can be placed over the core and the fabric layer is then placed onto this film. Another film of the same or similar composition is preferably applied to the top of the fabric. The assembly including the core, fabric layer, and the layers of thermoplastic film is then placed into a compression molding press which subjects the components to elevated heat and pressure. The films, fabric, and core are thereafter consolidated and fused into an integral panel shape. The total amount of film needed to fully bond, incorporate, and/or cover the fabric depends upon the thickness, porosity, and texture or the fabric. As a rule of thumb, the total film thickness should be about 0.3 to about 3.0 times the thickness of the fabric. One may use more film below or above the fabric to impart aesthetic appearances, e.g., texture, depth, etc.

In the most preferred construction, the fabric layer weave and the fiber construction of the core are chosen so that the melted film resin flows through the interstices in the fabric layer weaving to anchor the fabric to the panel. Additionally, the fibers of the fabric layer can be intertwined and bonded closely with the fibers of the core to increase the adhesion of the fabric layer to the core. It is further envisioned that the thermoplastic film can be substituted by an evenly distributed resin powder or a suitable adhesive to achieve the same result. The fabric, thus applied to one or both planar surfaces of the panel-like core, becomes the outermost layer of the composite material, and acts to overcome the problems of wrinkling, and a lack of an aesthetic appearance usually associated with conventional composite materials.

The polymer matrix composite materials of this invention are thermoformable, and can be used to produce molded articles ranging from suitcases to shoe supports. Referring to FIG. 7, a thermoforming method for producing a safety shoe toe protector is diagrammatically described. The composite material is heated in step 7(a), followed by placing the heated material onto a mold in step 7(b). Under heat and pressure, for example using vacuum forming or compression molding, the mold conforms the heated composite material to a given shape in step 7(c). In step 7(d), the die is opened, and the finished, thermoformed part—in this case, a safety shoe toe protector—is removed and cooled.

From the foregoing, it will be understood that this invention provides polymer matrix composites having a bonded fabric layer which can be thermoformed without wrinkling or distortion. The difference in the elasticity between the fabric layer and the thermoplastic composite core of this invention is sufficient so that when the mold is applied to thermoform the composite material, the fabric layer stretches to conform smoothly to the core over contours and the like. Although various embodiments have been illustrated, this was for the purpose of describing, and not limiting the invention. Various modifications will become apparent to one skilled in the art, and are considered within the scope of the attached claims.

Thermoplastic Orthopedic Brace and Method of Manufacturing Same

A lightweight orthopedic brace constructed from thermoshapable, thermoplastic composite laminate bars is provided by this invention. A novel method for easily shaping the bars that maintains the mechanical and structural integrity of the pre-shaped composite bars is also provided. The materials and processes described above for the composite panel embodiment are hereby incorporated by reference.

The terms "thermoplastic" and "fabric layer" are as defined above. The term "fiber-containing layer" is similar to fabric layer in that it means the layers used to build up a composite laminate within which fibers are contained. The terms "thermoshaping" or "thermoshapable" mean the ability or action of shaping an object that softens upon heating and resolidifies after cooling.

Figure 8:
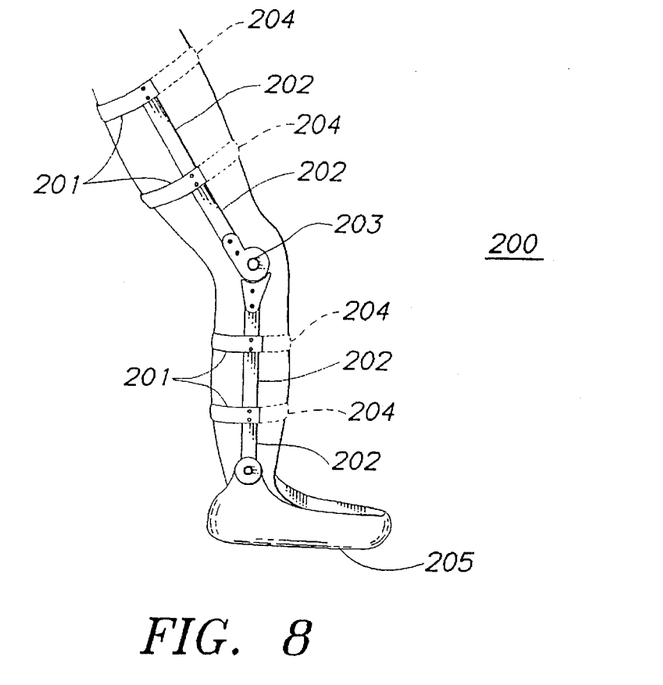
FIG. 8: is a side planar view of a knee orthopedic brace using thermoplastic composite bars of this invention as the structural components of the brace.

With reference to the Figures, the orthopedic brace embodiment of this invention is described in the following text. As illustrated in FIG. 8, an orthopedic brace 200 is constructed from a pair of upright bars 202 connected to a series of bands 201 which extend around the half circumference of the patient's upper or lower appendage. These upright bar/band structures are connected to a hinge mechanism 203 that is centered at the patient's joint to be supported, such as a person's knee, shown in FIG. 8. Flexible bands 204 are attached to the upright bars 202 to hold the brace on the patient's appendage. In a preferred embodiment, an orthotic support 205 can be attached to the brace providing support for the patient's hand or foot.

There clearly is a vast range of demands placed upon an orthopedic brace. For example, a child with a slightly injured elbow or knee would place minimal stress on the brace, while a heavy set young athlete with a dislocated knee would put severe demands on the brace and its materials. In this invention the orthopedic brace upright bars 202 and bands 201 are constructed from thermoplastic composite laminates.

The upright bar 202 is fabricated from a thermoplastic composite laminate containing multi-axial fiber orientation, with a substantial number of fibers along the bar 202 length. The fibers are impregnated with a suitable thermoplastic resin and consolidated into a composite laminate.

In order to withstand the dynamic and static stresses and strains typically found in an arm or leg brace, the fibers must have sufficiently high tensile and flexural strength and modulus respectively. The quantitative values desirable in the fiber are as follows:

|  | Minimum | Preferred |
|---|---|---|
| Tensile Strength (MPa) | 2500 | 3500 |
| Tensile Modulus (GPa) | 60 | 200 |
| Specific Tensile Strength* ($10^7$ cm) | 1.0 | 2.0 |
| Specific Tensile Modulus** ($10^9$ cm) | 0.23 | 1.0 |

*Specific Tensile Strength = Tensile Strength/Density
**Specific Tensile Modulus = Tensile Modulus/Density The type of fibers that could meet these described requirements include metal, carbon, glass, quartz and ceramic. While the aramid fibers meet the tensile requirement, they are less desirable since they tend to not have sufficient flexural properties to provide sufficient rigidity to the bar. As such, the aramid fiber is not the preferred primary fiber component of the bar. While a functional bar containing glass fibers could be made for a low demanding application with the minimum properties, the preferred properties are desirable for most applications.

For comparative purposes, the mechanical properties of metals and two types of fibers as used in thermoplastic bars are provided in the following table.

|  |  | Aluminum | Steel | Carbon | Low Modulus E-Glass |
|---|---|---|---|---|---|
| Tensile Strength | (MPa) | 275 | 1000 | 4100 | 3450 |
| Tensile Modulus | (GPa) | 68 | 207 | 227 | 72 |
| Density | (g/cm³) | 2.7 | 7.9 | 1.8 | 2.58 |
| Specific Tensile Strength | ($10^7$ cm) | 0.10 | 0.12 | 2.27 | 1.33 |
| Specific Tensile Modulus | ($10^9$ cm) | 0.25 | 0.26 | 1.26 | 0.28 |

The preferred fiber layers for the bars are carbon fibers, followed by glass fibers. This is because the high physical strength properties and extremely low specific gravity of the carbon fiber make the bar a very light weight and very strong brace component. While the low modulus carbon and E-Glass are stated in the above property table, other grades of carbon and glass can also be used.

Selection of the fiber-containing layer involves a balance between the expense of the components and the required performance of the composite structure system. Although the carbon fiber has been found to offer the best specific tensile strength and modulus, it is also possible to incorporate other fiber types in the laminate for various purposes, e.g., glass fiber to reduce the cost, or aramid fiber to alter the failure mode characteristics.

Since thermoshaping is a key element of the invention, the resin type to be selected is desirably a thermoplastic material. The thermoplastic resin should have sufficient mechanical properties to impart strength to the final composite laminate. For example, a softer resin, e.g., ethylene vinyl acetate or low density polyethylene, would make a weak composite which would be less desirable for the demanding requirements of a knee brace.

It has been found that the following properties of the resins are preferable to produce a bar with functional characteristics. Minimum and preferred property values are shown.

|  |  | Approximate Minimum Values | Preferred Values |
| --- | --- | --- | --- |
| Tensile Strength | (MPa) | 25.00 | 60 |
| Tensile Modulus | (GPa) | 1.200 | 2.0 |
| Flexural Modulus | (GPa) | 1.200 | 2.0 |

The resins that meet the minimal values include polypropylene, high density polyethylene, polyamide 12, certain polyurethanes and polyesters and their respective copolymers and derivatives. The preferred resins have been found to have generally high tensile and flexural modulus. These resins include polyamides such as Nylon 6, and Nylon 6,6, polymethyl metha acrylate (acrylic resins), polycarbonate, polyethylene terphathalate, polybutylene terphathalate, polyphenylene sulphide, high hardness polyurethanes, and their copolymers and derivatives. These listed resins only are given as examples. The invention is not meant to be restricted to named resins only.

The preferred resins were found to be Nylon 6 and polymethyl methacrylate in order to achieve high flexural modulus, while having a moderate melting point below 250° C. While resins such as polyphenylene-sulphide and polyetherimide provide very high mechanical properties, their melting points are over 275° C. Composites made with these resins would require special high temperature ovens that would not commonly be available to the general small orthopedic workshops.

Figure 9:
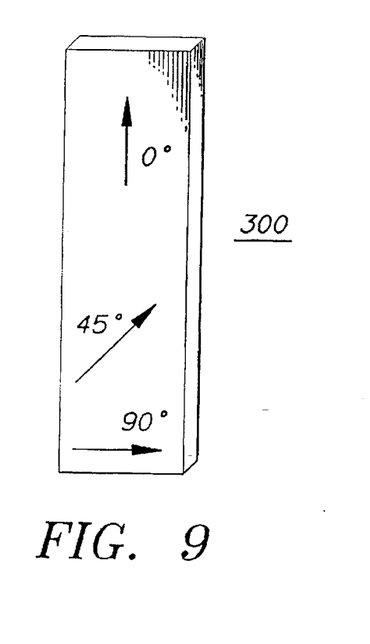
FIG. 9: is a front perspective view of one preferred fiber orientation of the fiber-containing layers within the composite bar.
Figure 10:
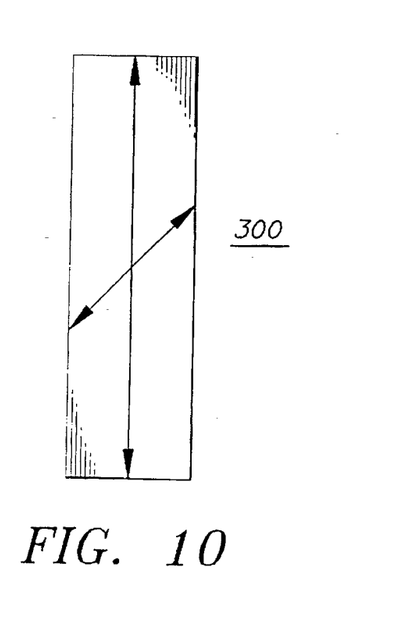
FIG. 10: is a front planar view of the preferred continuous length of the fiber-containing layers within the composite bar.

As previously discussed, the primary property required of the upright bar is high flexural strength and modulus. This is best achieved through continuous fiber lengths orientated in the upright composite bar 300 longitudinal or 0 degree direction, as shown in FIG. 9 and FIG. 10. A secondary property required of the upright bar is the need for high torsional resistance. Torsional strength is best achieved through orientation of a portion of the fibers in the 45 degree direction and possibly in the 90 degree direction, as illustrated in FIG. 9.

It has been found that in order to obtain the best functional performance in the bar, in terms of flexural properties, about 30% to 95% of the fibers can be oriented in the 0 degree direction, and preferably about 45% to 75% of the fibers in the 0 direction. The highest torsional resistance has been found to be achieved by having about 5% to 65% of the fibers in the 45 degree direction and preferably about 15% to 50% in the 45 degree direction. The fibers described as being oriented at 45 degrees may equally be in the 1 degree to 90 degree range. For example, some fibers may be oriented at about 30 degrees, some at about 45 degrees, and some at about 90 degrees. The objective is to have fibers in the non-zero direction to resist twisting forces imparted to the bar.

The length of the fibers in the bar is important, in that the critical factor is that the fiber layer within the bar must be substantially continuous. While attempts have been made to produce bars with long but discontinuous fibers, these systems result in very inefficient composites. Because the mechanical performance of the bar is predominantly obtained from the fibers, discontinuities or gaps in the fiber lengths results in lower mechanical properties.

Accordingly, the most preferred fibers, regardless of orientation, have a continuity from one edge of the bar to the opposite edge of the bar, as shown in FIG. 10. For example, the fibers in the 0 degree orientation would desirably extend from the lower end of the bar to upper end, while the fibers in the 45 degree orientation would extend from one side to the other side of the bar, as provided in FIG. 10.

As has been discussed earlier, the composite derives most of its mechanical properties from the fiber rather than the resin. It is therefore desirable to use a high volume content of fiber. A limitation to the volume of fiber layers is that there must be sufficient resin content to ensure uniform coating and wet-out of the fibers to provide integrity to the composite body. It has been found that the fiber volume content preferably is about in the 25% to 75% range to be of functional use in the bar. The preferred fiber volume content range was found to be about 30% to 55%.

The principle of the composite laminate fabrication is that the resin impregnated fibers are stacked in a multi-layer structure, with the fiber directions in each layer appropriately oriented. The structure is then consolidated under heat and pressure into a laminate. The laminate bar described by the present invention could be in the form of individual bars formed in a mold, or made from a large panel from which individual bars are subsequently cut.

The ideal method for shaping the composite laminate bar of this invention would include (1) permitting the bar to maintain a flat and rectangular shape during heating without lofting, (2) handling the bar handled with gloved hands, (3) placing the bar on the plaster cast of a leg, and (4) pressing down with reasonable hand pressure to a desired shape. The resulting shaped bar would maintain its original integrity, including its rectangular profile and mechanical properties. The novel invention method described herein practically achieves all the elements of the ideal method described above.

The preferred inventive method involves two physical components attached to the composite bar 300 prior to placing it in the oven. These components act as a mold to maintain the rectangular shape of the bar 300 during the heating and shaping process.

Figure 13:
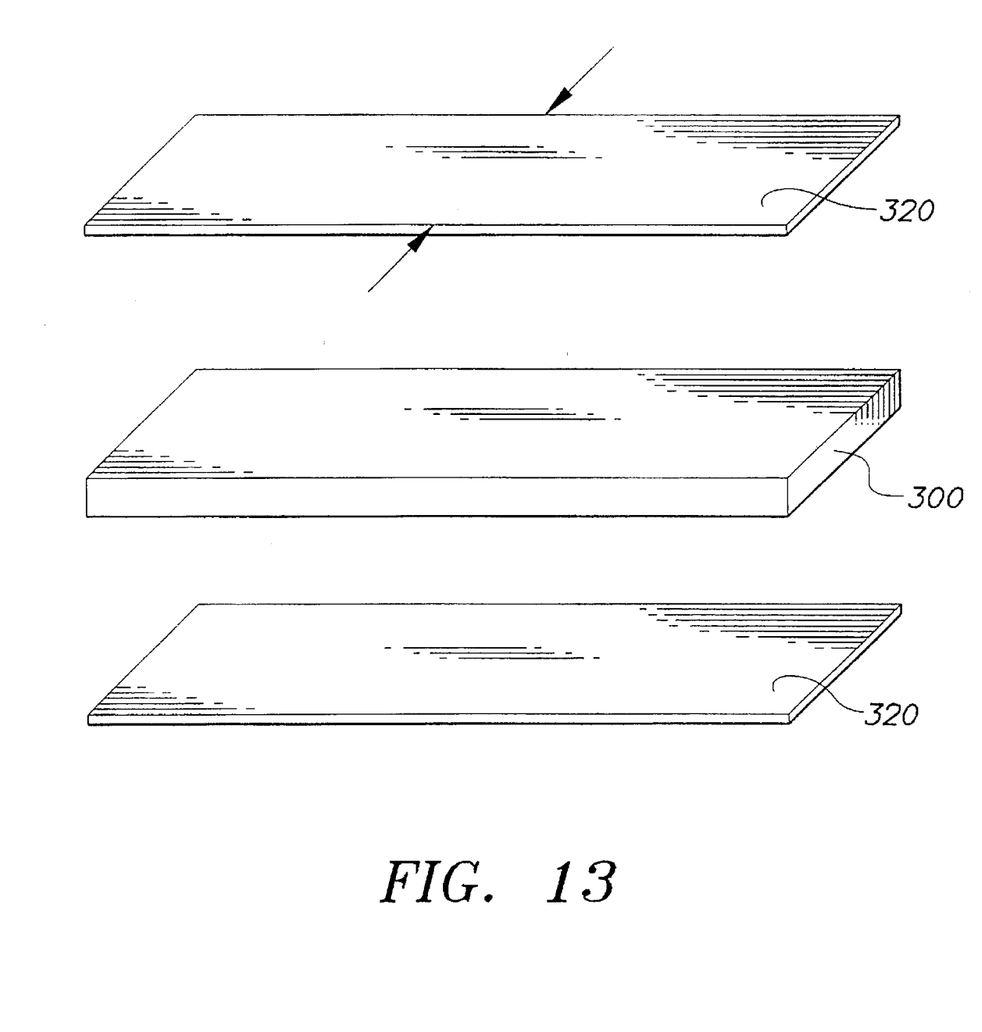
FIG. 13: is a side perspective view of the preferred sandwiching of the composite bar between molding strips for thermoshaping the composite bar.

Reference is now made to FIG. 13. The preferred molding strip 320, is a thin material in which its plane can be bent or flexed in the A-B direction (up or down). The molding strip 320 preferably does not bend in the A-C direction, or stretch in the A-D direction and most importantly, the molding strip 320 should not be compressed in the shown X-Y direction.

Figure 14:
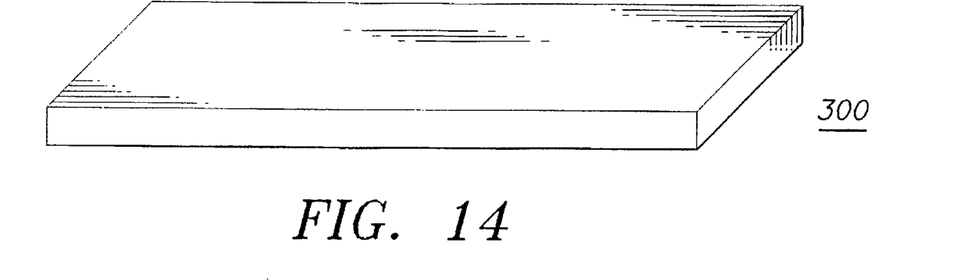
FIG. 14: is a side perspective view of a thermoplastic composite bar prior to thermoshaping.
Figure 15:
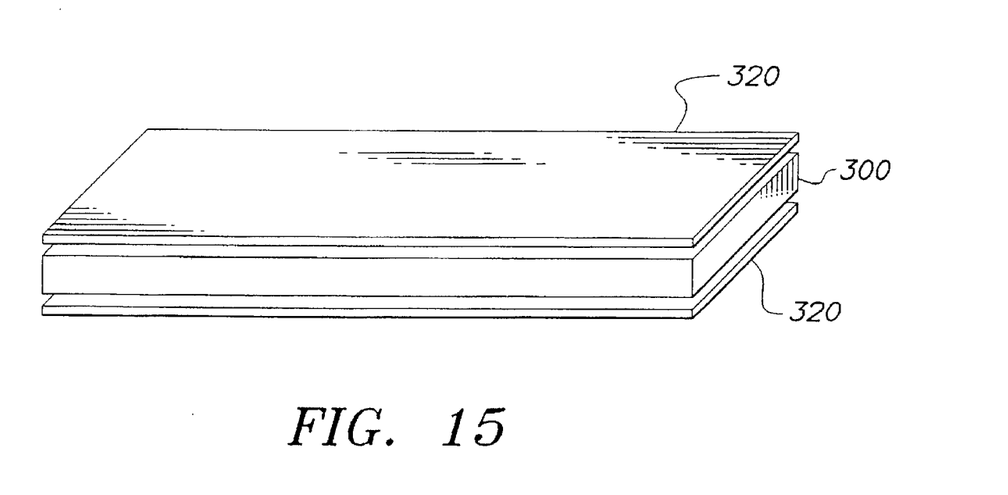
FIG. 15: is a side perspective view of a thermoplastic composite bar sandwiched between the two molding strips.

Two molding strips 320 can be placed on the wider sides of the bar 300, as shown in FIG. 14 and FIG. 15, to further control the molding process. When the bar is bent and shaped in the A-B direction, the molding strips 320 would bend with it.

Figure 16:
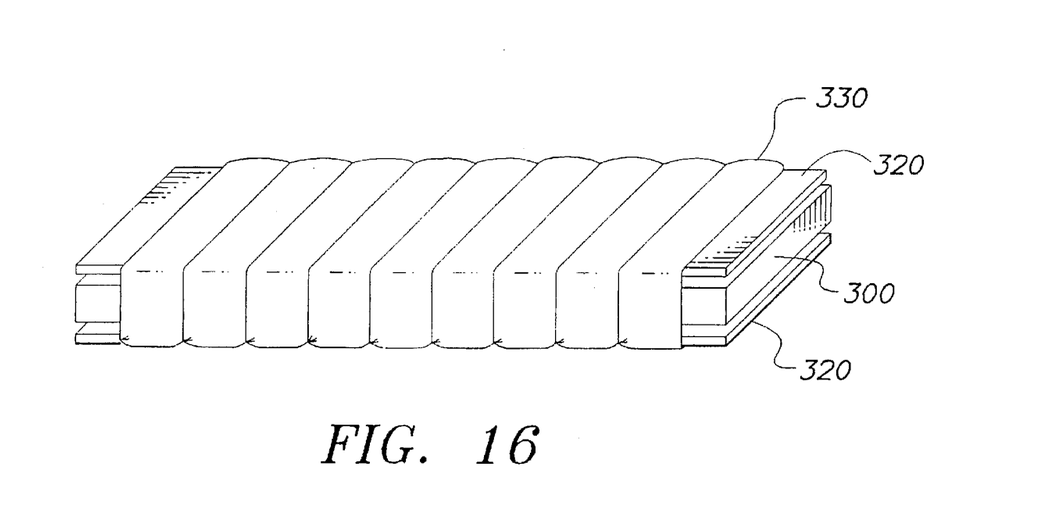
FIG. 16: is a side perspective view of a thermoplastic composite bar prepared within the invention method for thermoshaping.

A high temperature tape 330, with or without adhesive, can be spirally wrapped around the bar/strips sandwich, as illustrated in FIG. 16. The tape provides a jacket around the sandwich formed by the bar 300 and strips 320; holds the strips 320 in an intimate contact with the bar 300; and prevents sideways movement of the softened bar 300 (i.e., in the A-C direction shown in FIG. 13). Although heat shrink tubing could be used in place of the tape 330, it has been found to be less effective.

The resulting assembly of composite bar 300, molding strips 320 and tape 330 is a novel "mold" formed around the bar 300 to maintain the bar shape. The strips 320 maintain a smooth flat surface of the bar 300 at all times and allow controlled bending and shaping of the bar 300 in the A-B direction. It is important to note that because the strips 320 are desirably not capable of being compressed in the X-Y direction, the integrity of the bar shape is contained within the edges of the two strips 320.

A key property of the tape 330 is that at the shaping temperature it should not become soft and pliable. In a preferred embodiment, two layers of high temperature tape 330 should be tightly wrapped in a spiral fashion around the composite bar 300 held between the two molding strips 320. Each layer of the tape 330 is preferably disposed at cross angles to maintain the stability of the assembly. Where only one spiral layer of the tape 330 is used, the bar 300 may become slightly twisted.

Because the tape does not soften or stretch during the heating process, the bar is not allowed to loft. Accordingly, the original dimensions of the bar between the strips are maintained. Also because the tape is essentially nonstretchable, the body of the bar is prevented from sliding sideways in the A-C direction even when pressure is applied to shape the composite bar.

This simple method also facilitates the sliding of fiber layers in the longitudinal direction, i.e., A-D direction as shown in FIG. 13, without causing distortion of the bar. The ends of the bars are preferably open, and during bending, the fiber layers are free to slide within the rectangular mold (formed by strips and tape) in the A-D direction, so that no wrinkling or buckling occurs at the bottom surface of the bar, as shown in FIGS. 12–12(b).

A further advantage of this inventive method is in the relative insensitivity of the thermoshaping process to molding temperature. Without use of the inventive method mold, if the heating time was too short or the temperature was too low, the bar would tend to wrinkle or delaminate during the shaping process. Alternatively, if the heating time was too long or the temperature was too high, the bar would tend to lose its shape and become unacceptably deformed. By contrast, with the use of the strip/tape assembly method, the bar can be heated to a temperature slightly more than necessary to ensure thorough melting of the resin, and the bar will still maintain its integrity and shape.

The molding strip 320 can be constructed from metal or plastic. However, its melting or softening temperature should exceed that of the resin the composite bar. For a composite molding strip, the resin could be thermoset, such as epoxy or polyester. For a composite thermoplastic strip, the resin could be Nylon 6 or polyphylene sulphide. For the typical upright bar dimensions, as used for orthopedic braces, the preferred dimensions of the strip should be within the range of about 0.1–2.0 mm.

In a preferred embodiment, the molding strip 320 could have a similar coefficient of expansion as the composite bar 300, particularly along the bar length. This can be achieved, in part, by using fibers in the molding strip 320 which are similar to those used in the composite bar 300. A composite molding strip made of carbon, glass, ceramic or quartz fibers with a suitable temperature insensitive resin is found to be the preferred embodiment.

Figure 17:
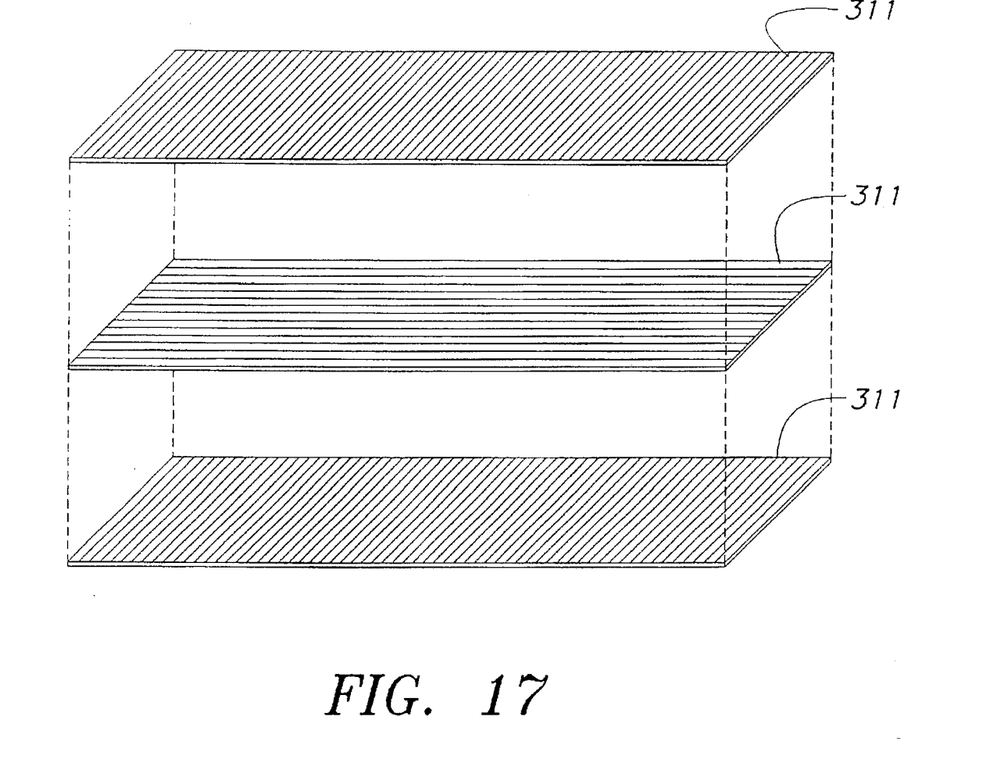
FIG. 17: is a side perspective blow-up view of a composite molding strip showing the preferred orientation of fiber-containing layers within the molding strip.
Figure 18:
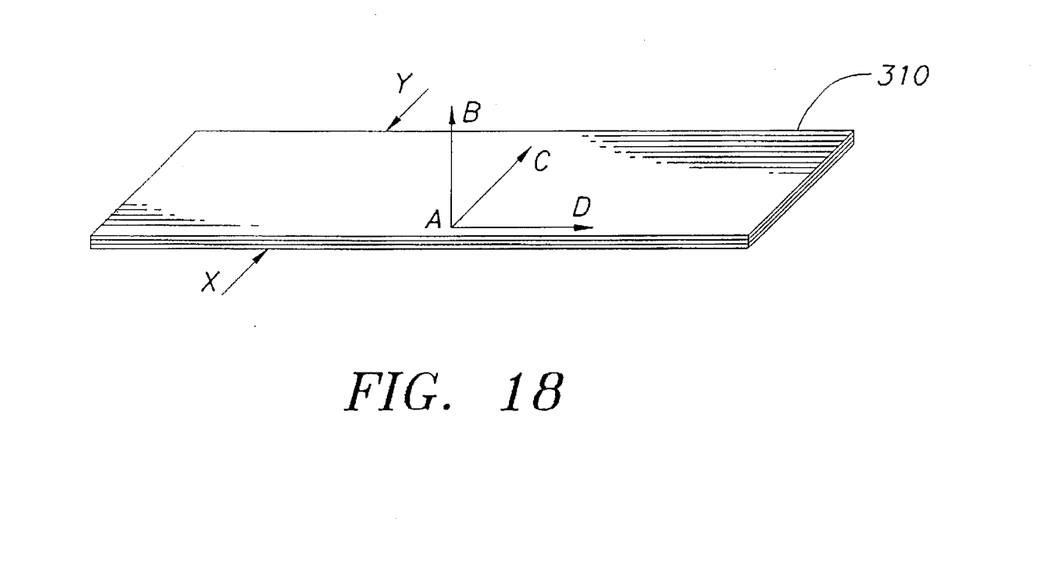
FIG. 18: is a side perspective view of a consolidated composite laminate molding strip.

For the preferred composite molding strip 320, the preferred fiber orientation is 90 degrees (i.e., A-C direction, as shown in FIG. 18). Alternatively, the majority of fibers could be oriented in the 90 degrees direction with less than 50% fibers at 0 degrees (i.e., A-D direction, shown in FIG. 18) to ensure some integrity to the strip, as shown in fiber layers 311 of FIG. 17. The fibers oriented at 90 degrees would prevent the compression of the strip in the X-Y direction and yet allow bending in the A-B direction. These fibers could be encapsulated by a suitable resin. The strip could also be made from woven fabric of the fibers and impregnated with suitable resin.

The tape 330 can be a thermoplastic tape, such as polyester, as long as its softening temperature is significantly higher than the temperature of the composite bar to be shaped. A polyester tape with softening temperature of about 250° C. works well on a composite bar made with Nylon 6 with a softening temperature of about 220° C. The tape 330 should be substantially nonstretchable and nonpliable at the softening temperature of the composite resin. Such tape materials may include polymerics, polymerics with reinforced fibers that are "non-stretching", e.g., glass, cotton, or tape made from fibers such as glass, cotton or polyester.

For composite bar dimensions typically used for orthopedic braces, the tape thickness should be in the range of about 0.01 mm–1.0 mm, and preferably be about in the 0.04 mm–0.4 mm range. The ideal thickness depends on the type of tape material used, e.g., a very stiff polyester tape needs to be about in the 0.04 mm range, while a woven glass fiber tape could be as thick as about 0.4 mm.

In a preferred embodiment, the taping means could be a heat-shrink tape. The advantage of a heat-shrink tape is that any relative looseness or sloppiness in wrapping over the sandwiched bar, is removed as the tape shrinks tightly around the bar. However, normal non-shrink tape works well when wrapped tightly.

In another embodiment, the taping means may have an adhesive on it. The presence of adhesive facilitates the wrapping process as the tape cannot become easily unravelled. However tape without adhesive works well, as long as the starting and ending portions of the wrapped tape are securely fastened by, for example, an adhesive.

The taping means could also be in a tubular form. The tube diameter must be large enough to be inserted over the sandwiched composite bar. The tube diameter could then be reduced in diameter to provide a mold over the bar. This could be achieved by using a heat-shrinkable polymeric tubing, or an appropriately knitted tube, e.g., glass, carbon or other fiber capable of withstanding the softening temperature of the bar resin.

EXAMPLE

A 450 mm long carbon/polyamide composite bar was sandwiched between two carbon/polyphenylene sulphide molding strips. This assembly was wrapped, without adhesive, with HI-SHRINK polyester tape, 19 mm in width and 0.05 mm in thickness, from Dunstone Company, Inc.

The starting and the ending portions of the above tape were secured with a high temperature adhesive tape. A first tape layer was spirally wrapped with an approximate 2.5 mm overlap at an angle of approximately +45°, and then a second layer was spirally wrapped similarly but in the −45° angle. The assembled bar was then placed in an oven at 230° C. for 12 minutes until softened.

The bar was removed using gloved hands, and placed on a plaster leg cast. In order to apply more uniform pressure on the bar, an aluminum strip 50 mm wide×0.4 mm thick and 500 mm long was placed on the bar. This thin aluminum strip was pliable and flexible. Hand pressure was applied on the aluminum strip to force the bar assembly to conform to the plaster cast. Slight pressure was also applied to ensure that the "compressive consolidation" of the bar was maintained particularly at the sections with sharp bends.

The composite bar/mold assembly was maintained in this position for 2 minutes, and then cooled in cold water for 3 minutes. The polyester tape and the molding strips were removed. The resulting shaped bar retained its original rectangular cross-section and maintained excellent consolidation.

Tests were conducted on the bars before and after shaping with the following results. For comparative purposes, the values for bars shaped without molding strips or tapes are also shown.

|  | Original Bar | Bar Shaped With Invented Method | Bar Shaped Without Invented Method |
| --- | --- | --- | --- |
| Flexural Break Load (N) | 2160 | 2150 | 1975 |
| Flexural Strength (MPa) | 669 | 572 | 387 |
| Flexural Modulus (GPa) | 50 | 44 | 20 |

The above values plainly show the benefit of using the invention method. About 85% of the preshaped composite bar mechanical properties are maintained using the inventive method while the bar shaped without the inventive method lost approximately 60% of its preshaped mechanical properties.

Accordingly, from this invention description, a lightweight thermoplastic orthopedic brace is provided along with a method of easily thermoshaping the composite laminate bars used in the orthopedic brace. This method maintains the structural and mechanical properties of the preshaped composite bar. Although several embodiments of the composite bar and method of manufacturing it have been illustrated, these embodiments were for the purpose of describing and not limiting the invention. Various modifications will become apparent to one skilled in the art, and are considered within the scope of the attached claims.

What is claimed is:

1. An orthopedic brace, comprising:

a mechanical joint for providing a degree of rotation to the joint of a patient's appendage;

first and second support bars affixed to said mechanical joint;

a plurality of shaped thermoplastic composite bands affixed to said first and second support bars respectively, said bands comprising at least a pair of laminated fiber-containing layers including a thermoplastic resin having a flexural modulus of at least about 1.2 GPa and a thermoplastic melting point of less than about 275° C.; and retaining means for grasping distal and medial portions of said appendage.

2. An orthopedic brace, comprising:

a mechanical joint for providing a degree of rotation to the joint of a patient's appendage;

first and second support bars affixed to said mechanical joint;

a plurality of shaped thermoplastic composite bands affixed to said first and second support bars respectively, said bands comprising at least a pair of laminated fiber-containing layers including a thermoplastic resin having a flexural modulus of at least about 1.2 GPa and a thermoplastic melting point of less than about 275° C.; and a plurality of retaining straps for forming a looped structure with said first and second thermoplastic composite supports for grasping distal and medial portions of said appendage located on opposite sides of the patient's joint.

3. The orthopedic brace of claim 2 wherein said thermoplastic melting point is less than about 250° C.

4. The orthopedic brace of claim 2 wherein said thermoplastic composite bands comprise a thermoplastic resin selected from the group comprising polyamide, polymethyl methacrylate, polycarbonate, polyethylene terphathalate, polybutylene terphathalate, polyphenylene sulphide, polyurethane, and their respective copolymers, compounds and derivatives.

5. The orthopedic brace of claim 2 wherein said laminated fiber-containing layers comprise fibers selected from the group comprising metal, carbon, glass, quartz, aramid, ceramics and mixtures thereof.

6. The orthopedic brace of claim 2 wherein said thermoplastic resin has a tensile strength of at least about 25 MPa.

7. The orthopedic brace of claim 5 wherein a portion of said fibers in a first of said laminated fiber-containing layers are disposed to extend substantially continuously from one end of said first layer to an opposite end of said first layer.

8. The orthopedic brace of claim 2 wherein at least about 30%–95% of the fibers in said pair of laminated fiber-containing layers are oriented along the length of said first and second support bars, and a remaining portion of said fibers are oriented in directions other than along the length of said first and second support bars.

9. An orthopedic brace, comprising, a first pair of upright thermoplastic composite bars rigidly joined to each other by a first plurality of shaped thermoplastic composite bands, said first pair of upright bars and said first plurality of shaped bands forming a first cradle structure;

a second pair of upright thermoplastic composite bars rigidly connected to each other by a second plurality of shaped thermoplastic composite bands, said first and second plurality of shaped thermoplastic composite bands comprising at least a pair of laminated fiber-containing layers including a thermoplastic resin having a flexural modulus of at least about 1.2 GPa and a thermoplastic melting point of less than about 275° C., said second pair of upright bars and said second plurality of shaped bands forming a second cradle structure;

one end of the first cradle structure pivotally connected to one end of the second cradle structure by a mechanical joint, thereby forming a support for a person's appendage with the mechanical joint centered at the appendage joint to be supported; and, on each cradle structure, a plurality of flexible straps attached at one end to one of the upright bars and attachable at the other end of said flexible strap to the other upright bar, whereby said cradle structures are maintainable around and supporting a person's appendage.

10. The orthopedic brace of claim 9, further comprising, an orthotic support attached to the end of the second cradle structure to maintain and brace a patient's hand or foot.

11. The orthopedic brace of either claim 9, wherein the mechanical joint is fabricated from metal.

* * * * *